United States Patent
Landis et al.

(10) Patent No.: US 9,381,317 B2
(45) Date of Patent: *Jul. 5, 2016

(54) HIGH FLOW THERAPY ARTIFICIAL AIRWAY INTERFACES AND RELATED METHODS

(71) Applicants: Robert M. Landis, Mountainside, NJ (US); Charles A. Lewis, Carrabelle, FL (US); Louis Javier Collazo, Lauderdale by the Sea, FL (US)

(72) Inventors: Robert M. Landis, Mountainside, NJ (US); Charles A. Lewis, Carrabelle, FL (US); Louis Javier Collazo, Lauderdale by the Sea, FL (US)

(73) Assignee: Mergenet Medical, Inc., Coconut Creek, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,572

(22) Filed: Dec. 17, 2012

(65) Prior Publication Data

US 2013/0104901 A1 May 2, 2013

Related U.S. Application Data

(63) Continuation of application No. 12/347,409, filed on Dec. 31, 2008, now Pat. No. 8,333,199, which is a (Continued)

(51) Int. Cl.
*A61M 16/06* (2006.01)
*A61M 16/04* (2006.01)

(Continued)

(52) U.S. Cl.
CPC ....... *A61M 16/0666* (2013.01); *A61M 16/0057* (2013.01); *A61M 16/0493* (2014.02);

(Continued)

(58) Field of Classification Search
CPC . A61M 16/06; A61M 16/0666; A61M 15/08; A61M 16/12; A61M 16/202; A61M 16/0677; A61M 16/125; A61M 16/04; A61M 16/0463; A61M 16/0488; A61M 16/0688; A61M 16/0497; A61M 16/0672; A61M 16/085; A61M 16/0858; A61M 16/00; A61M 16/08; A61M 16/0063; A61M 16/0069; A61M 16/108; A61M 16/1085; A61M 16/1095; A61M 16/161; A61M 16/009; A61M 25/02; A61M 1/00; A61M 1/0062; A61M 5/142; A61M 5/172; A61M 15/0028; A61M 15/0033; A61M 16/0493; A62B 18/08; A62B 18/02; A62B 7/00; A62B 23/06; A62B 23/00; A62B 18/00; A62B 7/10; B29C 33/48; B29C 41/14; B29C 41/22; B29C 33/485; A61B 5/087; A61B 5/4818; A61B 5/6819; A61B 5/097; A61B 5/08; A61B 5/085; A61B 5/411; A61B 5/0836; A61B 5/682; A63B 33/00; G06Q 50/22; G06Q 50/24
USPC ............... 128/200.24, 848, 858, 857, 200.26, 128/203.22, 206.11, 206.18, 206.28, 128/206.29, 207.13, 207.14, 207.18; 606/191, 196, 198, 199

See application file for complete search history.

(56) References Cited

U.S. PATENT DOCUMENTS 1,383,502 A * 7/1921 Vultee ........................... 604/279
3,516,410 A * 6/1970 Hakim ........................... 604/268

(Continued)

*Primary Examiner* — Annette Dixon
(74) *Attorney, Agent, or Firm* — Adam C. Underwood

(57) ABSTRACT

Embodiments of the present invention provide a device, system and method for providing high flow therapy interfaces for use in the treatment of respiratory conditions and in assisted respirations. A nasal cannula for delivery of respiratory gases supplied from a respiratory gas delivery system that includes at least one nasal insert that includes a lumen for the supplied respiratory gases from the respiratory gas delivery system, at least one flange coupled to the at least one nasal insert and configured to partially impede the egress of respiratory gasses delivered to an upper airway of a patient, where the flange includes a top surface defining a corresponding top surface area and where the flange further includes at least one slot that defines a corresponding implicit surface area, the top surface area of the top surface being substantially greater than the implicit surface area of the at least one slot is provided.

26 Claims, 14 Drawing Sheets

Related U.S. Application Data continuation-in-part of application No. 11/638,981, filed on Dec. 14, 2006, now Pat. No. 8,333,194, which is a continuation-in-part of application No. 11/520,490, filed on Sep. 12, 2006, now abandoned, application No. 13/717,572, which is a continuation-in-part of application No. 11/999,675, filed on Dec. 6, 2007, now Pat. No. 8,522,782.

(60) Provisional application No. 61/009,702, filed on Dec. 31, 2007, provisional application No. 60/716,776, filed on Sep. 12, 2005, provisional application No. 60/750,063, filed on Dec. 14, 2005, provisional application No. 60/792,711, filed on Apr. 18, 2006, provisional application No. 60/852,851, filed on Oct. 18, 2006.

(51) Int. Cl.
*A61M 16/10* (2006.01)
*A61M 16/12* (2006.01)
*A61M 16/16* (2006.01)
*A61M 16/00* (2006.01)

(52) U.S. Cl.
CPC ......... *A61M16/0677* (2014.02); *A61M 16/125* (2014.02); *A61M 16/1075* (2013.01); *A61M 16/12* (2013.01); *A61M 16/16* (2013.01); *A61M 2016/0024* (2013.01); *A61M 2016/0027* (2013.01); *A61M 2016/1025* (2013.01); *A61M 2202/0208* (2013.01); *A61M 2210/0618* (2013.01); *A61M 2210/0625* (2013.01)

(56) References Cited

U.S. PATENT DOCUMENTS

| | | | | |
|---|---|---|---|---|
| 4,054,133 | A | * | 10/1977 | Myers .................. 128/204.26 |
| 4,156,426 | A | * | 5/1979 | Gold .................... 128/204.18 |
| 4,248,218 | A | * | 2/1981 | Fischer ................ 128/204.18 |
| 4,648,398 | A | * | 3/1987 | Agdanowski et al. ... 128/207.18 |
| 4,915,105 | A | * | 4/1990 | Lee ...................... 128/205.27 |
| 5,099,836 | A | * | 3/1992 | Rowland et al. ........ 128/204.23 |
| 5,322,062 | A | * | 6/1994 | Servas .................. 128/207.14 |
| 5,743,256 | A | * | 4/1998 | Jalowayski ............ 128/201.18 |
| 8,225,796 | B2 | * | 7/2012 | Davenport et al. ...... 128/207.18 |
| 8,333,199 | B2 | * | 12/2012 | Landis et al. .......... 128/207.18 |
| 2005/0066976 | A1 | * | 3/2005 | Wondka ................ 128/207.18 |
| 2013/0019870 | A1 | * | 1/2013 | Collazo et al. ......... 128/205.24 |

* cited by examiner

HIGH FLOW THERAPY ARTIFICIAL AIRWAY INTERFACES AND RELATED METHODS

CROSS-REFERENCE TO RELATED APPLICATIONS

This application is a continuation of U.S. patent application Ser. No. 12/347,409, filed Dec. 31, 2008, now U.S. Pat. No. 8,333,199, which claims the benefit of U.S. Provisional Patent Application Ser. No. 61/009,702, filed on Dec. 31, 2007, and U.S. patent application Ser. No. 11/999,675, filed Dec. 6, 2007, now U.S. Pat. No. 8,522,782, which is a continuation-in-part of U.S. patent application Ser. No. 11/638,981, filed on Dec. 14, 2006, now U.S. Pat. No. 8,333,194, which is a continuation-in-part application of U.S. patent application Ser. No. 11/520,490, filed on Sep. 12 2006, which claims the benefit of U.S. Provisional Patent Application Ser. No. 60/716,776, filed Sep. 12, 2005, U.S. Provisional Patent Application Ser. No. 60/750,063, filed on Dec. 14, 2005; U.S. Provisional Patent Application Ser. No. 60/792,711, filed on Apr. 18, 2006; and U.S. Provisional Patent Application Ser. No. 60/852,851, filed on Oct. 18, 2006, the entirety of all of which are incorporated by reference herein.

BACKGROUND

1. Statement of the Technical Field

The present disclosure relates generally to respiratory interfaces, and more particularly to the field of respiratory medicine and to devices for use in delivering respiratory gases for therapeutic effect in high flow therapy.

2. Description of the Related Art

High flow therapy (HFT), also known as nasal insufflation, allows a large volume of respiratory gases to be administered for therapeutic use. The cannula for selected HFT devices is designed for high flow rates and to fit loosely in the nares of a patient so that the cannula does not form a seal. Since HFT is traditionally flow based (the flow rate is set), a seal could cause development of high and possibly dangerous pressures to form. Moreover, a seal may prevent proper exhalation.

Respiratory gas at these high flow rates is typically heated and humidified for patient comfort. The breathing gas may be room air or a mixture of air and oxygen.

Nasal cannulas are presently used for delivery of HFT, and it is reported that flow rates at these high levels generate pressures in the upper airway of a patient. The level of upper airway pressure generated during HFT using a standard nasal cannula is dependent on the size of the cannula and the open area around the cannula inside the nostril. For any size cannula, the level of upper airway pressure will vary according to the shape and size of the patient's nostrils. The flow rate of the gasses and the velocity of the flow also can affect airway pressures. A patient with large nares would have a wider orifice and thus a lower pressure would be created than a patient with the same cannula and smaller nares. The pressure created in the upper airway is reported to have a therapeutic effect for certain respiratory conditions and sleep disorders. Consequently, during HFT, it may be desirable to control and increase the pressure in upper airways of the patient.

The airway pressures of patients are rarely, measured or regulated during HFT due to the lack of a conveniently available device or system for clinicians to use. The usual practice is for clinicians to administer HFT with flow rates within the patient's comfort zone and then monitor vital signs, oxygen saturation, and other relevant parameters. There are, however, devices in development that can measure the airway pressures of a patient during HFT. These HFT devices point to the need for new types of patient interfaces e.g., nasal cannula that maximize control and safety in the development of airway pressures during HFT.

Moreover, some patients may be mouth breathers. With a patent nasal passage, a nasal cannula for HFT will create some upper airway pressure when a patient is breathing through the mouth; however, the created pressure will not be as high as the pressure of isolated nasal breathing. As such, mouth breathing is a further limitation to creating upper airway pressures which may be desirable for use in therapy. Nasal insufflation may have low efficacy in patients with nasal congestion or poorly defined nasal passages.

SUMMARY

Embodiments of the present invention address deficiencies of the art in respect to patient interfaces and provide a novel and non-obvious device, system and method for providing patient interfaces for use with a non-sealing respiratory gas delivery system. In an embodiment of the invention, a nasal cannula for delivery of respiratory gases supplied from a respiratory gas delivery system that includes at least one nasal insert that includes a lumen for the supplied respiratory gases from the respiratory gas delivery system, at least one flange coupled to the at least one nasal insert and configured to partially impede the egress of respiratory gasses delivered to an upper airway of a patient, where the at least one flange includes a top surface defining a corresponding top surface area and where the at least one flange further includes at least one slot that defines a corresponding implicit surface area, the top surface area of the top surface being substantially greater than the implicit surface area of the at least one slot is provided. In another aspect of the embodiment, the at least one nasal insert includes an upper nasal insert portion and a lower nasal insert portion divided by the flange.

In yet another embodiment, a nasal cannula for delivery of respiratory gases supplied from a respiratory gas delivery system includes at least one nasal insert that includes a lumen for the supplied respiratory gases from the respiratory gas delivery system, at least one flange coupled to the at least one nasal insert, the at least one flange configured to partially impede the egress of respiratory gasses delivered to an upper airway of a patient, where the at least one flange includes a top surface defining a corresponding top surface area, where the at least one flange further includes at least one slot defining a corresponding implicit surface area, the top surface area of the top surface being substantially greater than the implicit surface area of the at least one slot and where the flange does not include a lumen to deliver the supplied respiratory gases from the respiratory gas delivery system.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

The present disclosure relates to a design of nasal cannula with features to enhance airway pressures without creating a seal around the cannula in the nares. The design also takes into consideration the need for safety and thereby avoids creation of a seal around the cannula inside the nares.

Certain configurations utilize a dual lumen approach where one lumen is for the gas flow and the other lumen is used to measure airway pressures. The capability to monitor airway pressures includes the desire to have greater control over airway pressures, and the ability to increase them.

In an embodiment of the invention, a nasal cannula for delivery of respiratory gases supplied from a respiratory gas delivery system that includes at least one nasal insert that includes a lumen for the supplied respiratory gases from the respiratory gas delivery system, at least one flange coupled to the at least one nasal insert and configured to partially impede the egress of respiratory gasses delivered to an upper airway of a patient, where the at least one flange includes a top surface defining a corresponding top surface area and where the at least one flange further includes at least one slot that defines a corresponding implicit surface area, the top surface area of the top surface being substantially greater than the implicit surface area of the at least one slot is provided. In another aspect of the embodiment, the at least one nasal insert includes an upper nasal insert portion and a lower nasal insert portion divided by the flange is provided. In another aspect of the embodiment, the flange has a shape selected from the group consisting of a slotted, vented or slitted design and configured to partially impede the egress of respiratory gasses, is provided.

In yet another embodiment, a high flow therapy interface includes at least one nasal cannula and at least one oral interface in fluid communication with the at least one nasal cannula, the oral interface including at least one port for delivery of respiratory gases to the mouth of a patient. In yet another embodiment, an oral interface for delivery of high flow therapy to the mouth of a patient is provided. In another aspect of this embodiment, the oral interface can include a gas diffuser that includes a terminus housing having a plurality of holes to allow the delivery of respiratory gases.

Airway pressures can be generated by decreasing the gas bypass area between the cannula and the inner wall of the nostril. The decreased gas bypass area between the cannula and the inner wall of the nostril can be accomplished by using a cannula that has larger nostril inserts. Another method of generating airway pressures includes placing an impeder ring on the cannula. The impeder ring can be a spongy material that allows some gas to flow through it.

Figure 1:
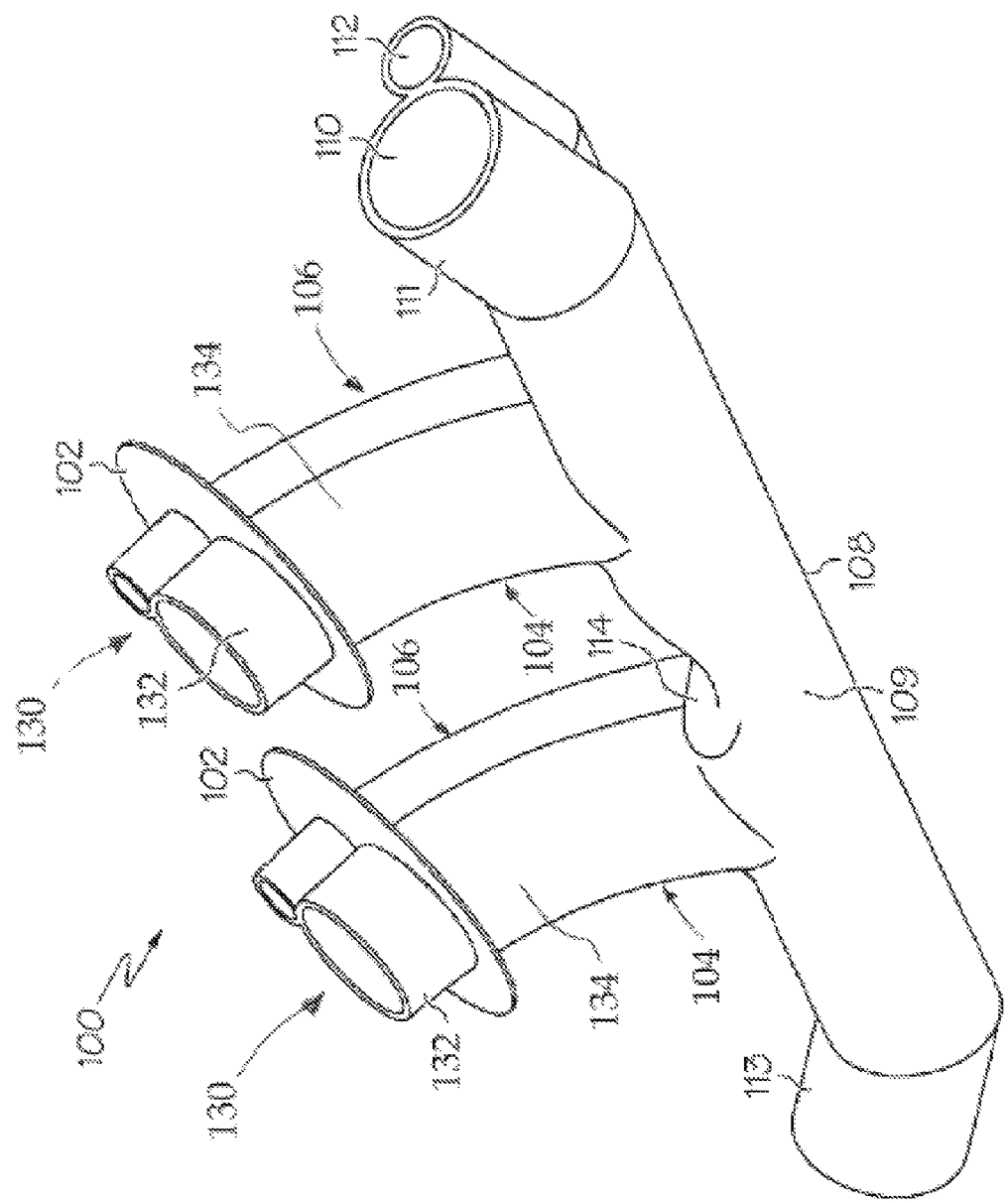
FIG. 1 is a perspective view of a dual lumen nasal cannula with a flange according to a particular embodiment of the invention.

A cannula 100 according to an aspect of the present disclosure is shown in FIG. 1. As may be understood from this figure, in this embodiment, the cannula 100 includes a soft flexible flange 102 that extends outward around the circumference of a gas supply conduit 104 and a pressure conduit 106. Flange 102 can be configured to flex and fit inside of the nostril of a patient or may fit up to the nasal alla. Flange 102 can be designed to be sufficiently flexible enough that it will not form a seal or stop the flow of gasses to and from the upper airway of a patient. Flange 102 can act as a partial barrier to the flow exiting the nasal passageway of a patient. This barrier action of flange 102 facilitates the generation of airway pressures while allowing sufficient air flow and avoiding the creation of a seal. The cannula 100 can include an interface body 108 that includes a hollow elongated tubular base portion that can include a central portion 109, a first end portion 111 and a second end portion 113. The first and second end portions 111, 113 can be angled relative to the central portion as illustrated in FIG. 1. In embodiments, the cannula 100 can include gas delivery inlets 110 and pressure sensing conduits 112 as illustrated and adjacent to the first end portion 111.

Additionally, the cannula 100 can include a gas delivery inlet 110 and a pressure sensing conduit 112 adjacent to the second end portion 113. Cannula 100 further can include an area 114 to prevent pressure on the nasal spine. In this embodiment, cannula 100 includes a separate gas supply conduit 104 (304) and a pressure conduit 106 (306) for insertion into the nostrils of a patient. As illustrated in FIG. 1, the gas supply conduit 104 (304) and pressure conduit 106 (306) form a nasal insert 130. Nasal insert 130 can include an upper nasal insert portion 132 and a lower nasal insert portion 134 which are delineated, divided and/or separated by the flange 102.

Figure 2:
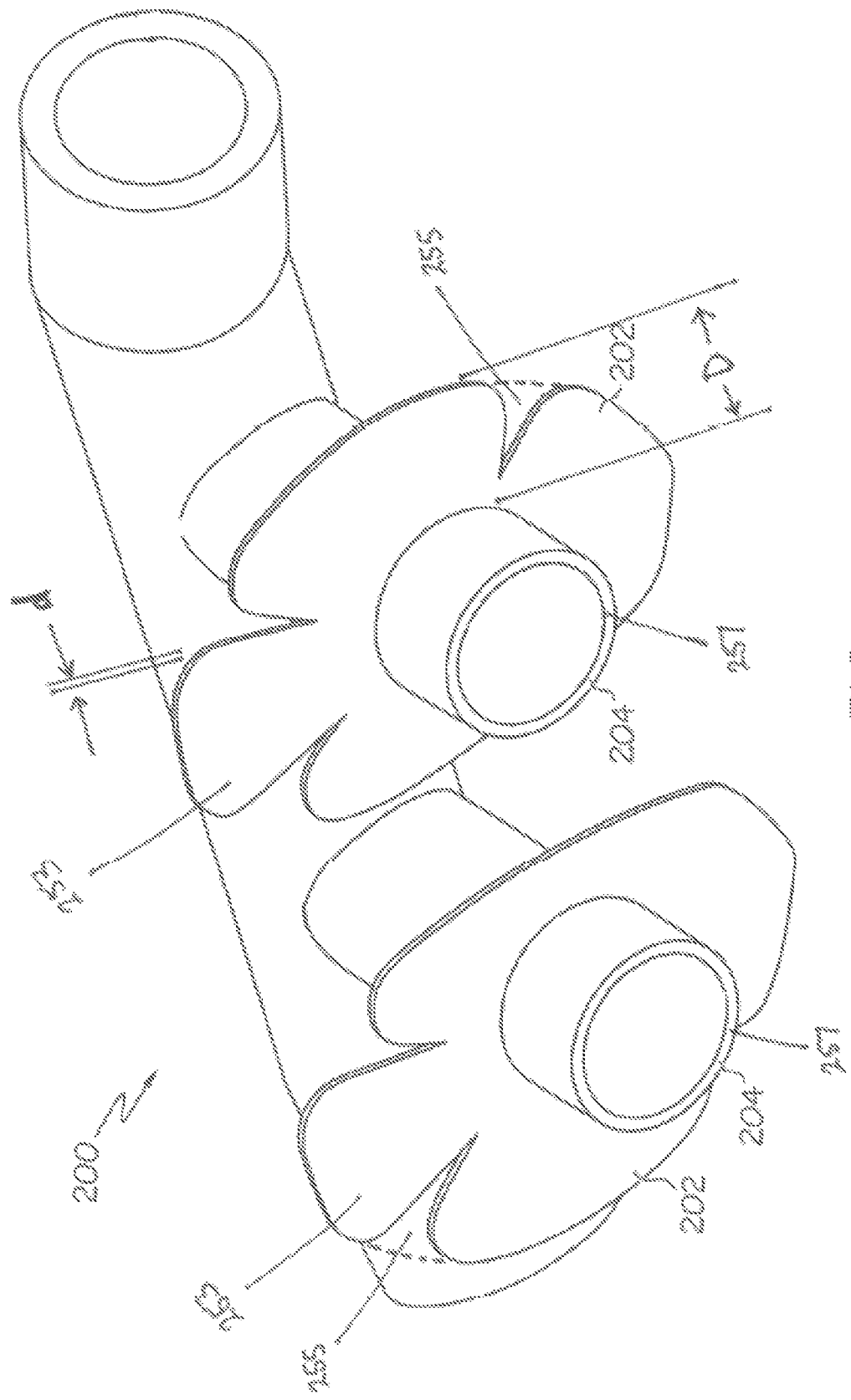
FIG. 2 is a perspective view of a single lumen nasal cannula with a lobulated flange, which is constructed in accordance with an embodiment of the present invention.

FIG. 2 illustrates a single lumen nasal cannula 200 with a gas supply conduit 204 with a length in an axial direction and a slotted or lobulated flange 202 which is configured to help avoid a seal in the nose of a patient. This feature can be created by providing fissures or slits in the flange 202 and thereby further preventing the flange's ability to seal the nostril around the gas supply cannula 204. The slotted or lobulated flange 202 advantageously provides a mechanism to restrict the flow of exhalation gases without creating a seal in the nostrils of a patient. Furthermore, the slotted or lobulated flange 202 provides a way to control the amount of pressure created in the upper airway passage of a patient. In embodiments, vents (not shown) can be placed in the flange 202 to function in a similar fashion to the fissures or slits of flange 202. As shown in FIG. 2, flange 202 has a first distance D measured from the circumference of the conduit 204 to any outer edge of flange 202, and flange 202 a second thickness distance d. As shown in FIG. 2 it is referred that first distance D be greater than second distance d. Flange 202 can have a flange top surface 253 that has a first surface area and that is substantially parallel to a conduit top surface 257 on the as SU 1 conduit 204. As shown in FIG. 2, flange 202 can have at least one slot 255 that has an implicit second surface area, where the understood outer edge of the slot 255 is illustrated in FIG. 2 by dashed lines. As is clearly shown in FIG. 2, the surface area of the top surface 253 is greater than the implicit surface area of slot 255.

Figure 3:
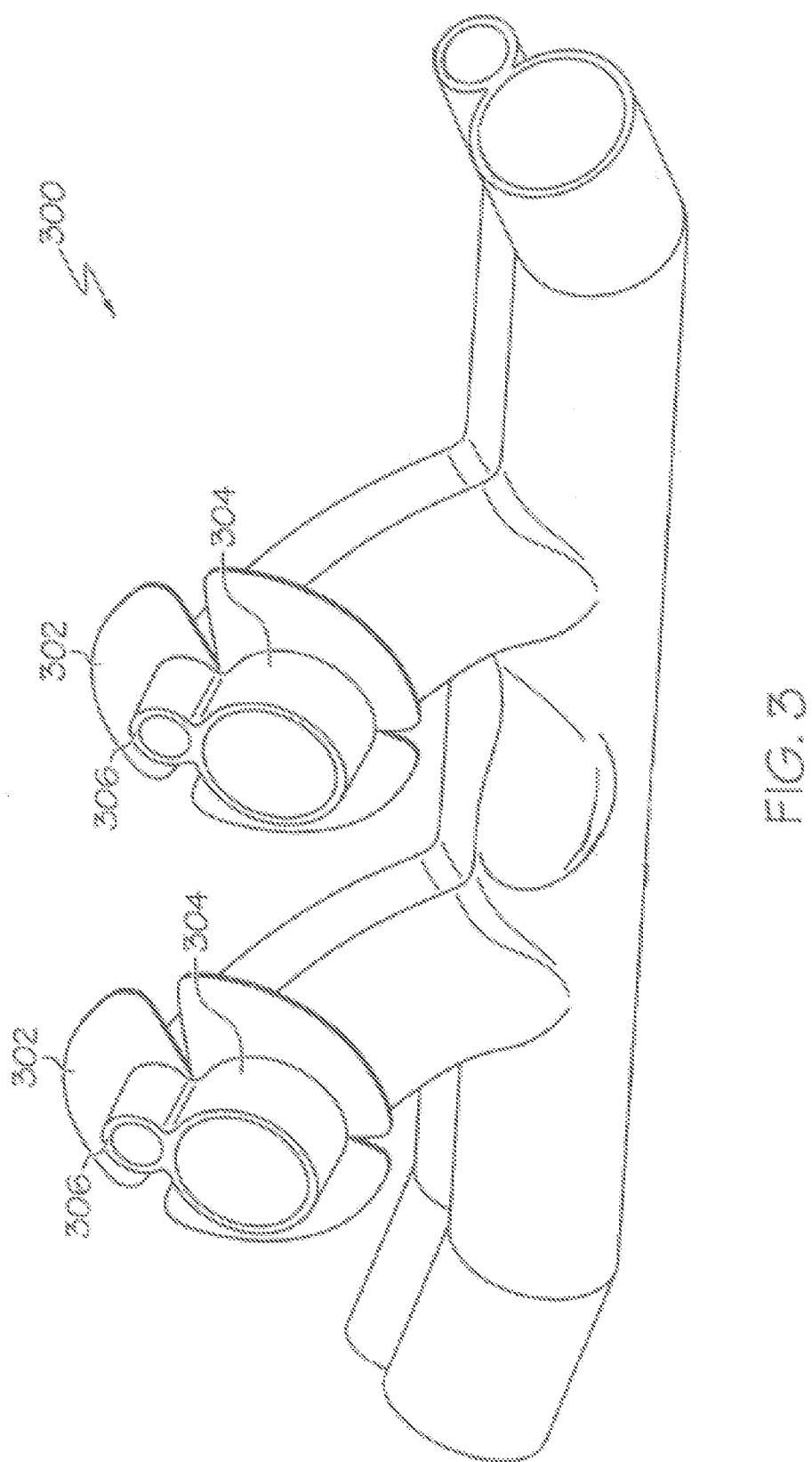
FIG. 3 is a perspective view of a dual lumen nasal cannula with a flange retention structure for the attachment of flanges, which is constructed in accordance with an embodiment of the present invention.
Figure 4:
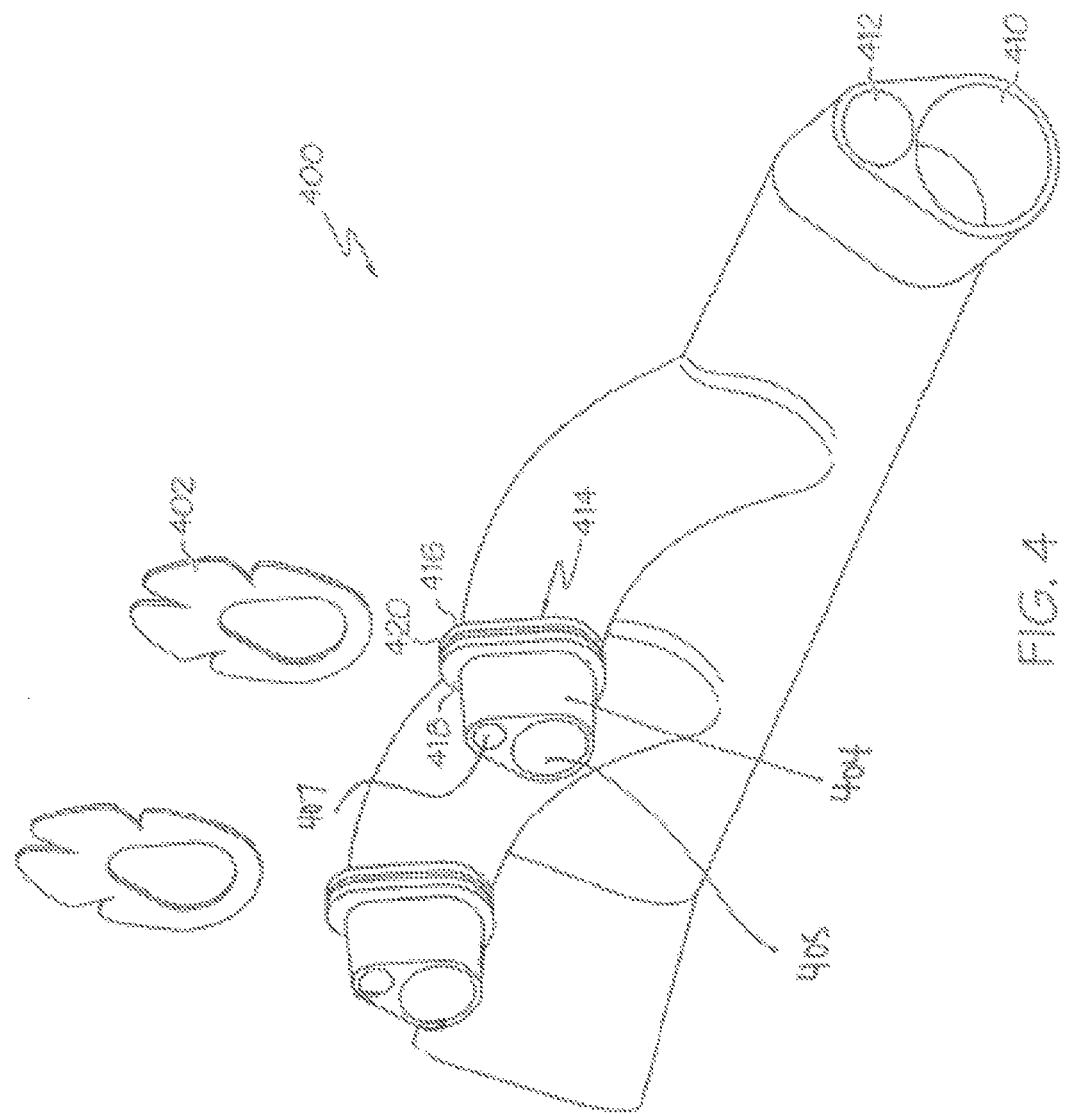
FIG. 4 is another perspective view of a dual lumen nasal cannula with a flange retention structure for the attachment of flanges, which is constructed in accordance with an embodiment of the present invention.

FIG. 3 illustrates a cannula 300 similar to the cannula 100 of FIG. 1 where the flange 302 is lobulated or slitted. In embodiments, the flanges 102, 202, 302 can be made separately and configured to fit onto a cannula or other artificial airway interface, which would provide for different flange sizes to be used based on the airway pressure desired and the nostril size of a patient. Separate flanges can also aid in ease of manufacture and further can allow selection of different flange thicknesses, or different materials to provide better control of flange flexibility. The shape of the flange can be selected from the group consisting of a slotted, vented or slitted design. FIG. 4 illustrates a cannula 400 that includes at least one single combination cannula insert 404 that includes gas supply orifice 405 and pressure orifice 407, which are in communication with gas supply inlet 410 and pressure sensing conduit 412, respectively. As illustrated in FIG. 4, the single combination cannula insert 404 can have an oval shape. The use of a combination cannula insert 404 can provide for greater ease of attachment and detachment of an impeder flange 402. Cannula 400 can include a flange retention structure 414. The flange retention structure or connector 414 can include a front stop 416, a backstop 418 and a flange groove 420 disposed between the front stop 416 and back stop 418 for receiving an impeder flange 402. In embodiments, the flange backstop 418 can be made with a somewhat larger ring to help prevent the flange 402 from passing too far down the length of the combination cannula insert 404 for ease of placement. In embodiments, the flanges 402 can be made of an elastic material which would resist disengagement after placement.

Figure 5:
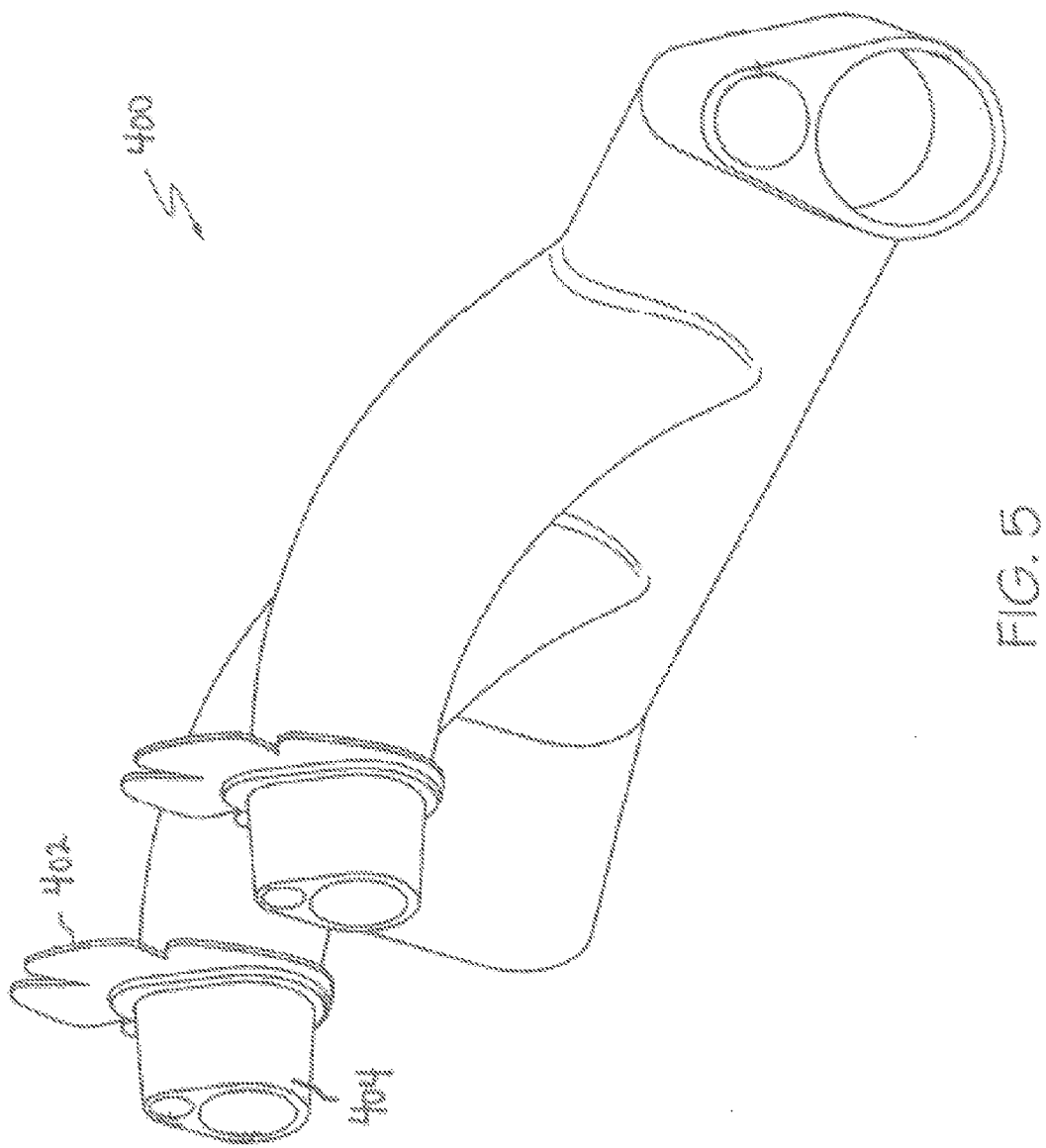
FIG. 5 is another perspective view of a dual lumen nasal cannula with a flange retention structure for attachment of flanges illustrated, which is constructed in accordance with an embodiment of the present invention.

FIG. 5 illustrates cannula 400 with the at least one impeder flange 402 in place on a combination insert cannula 404.

Figure 6:
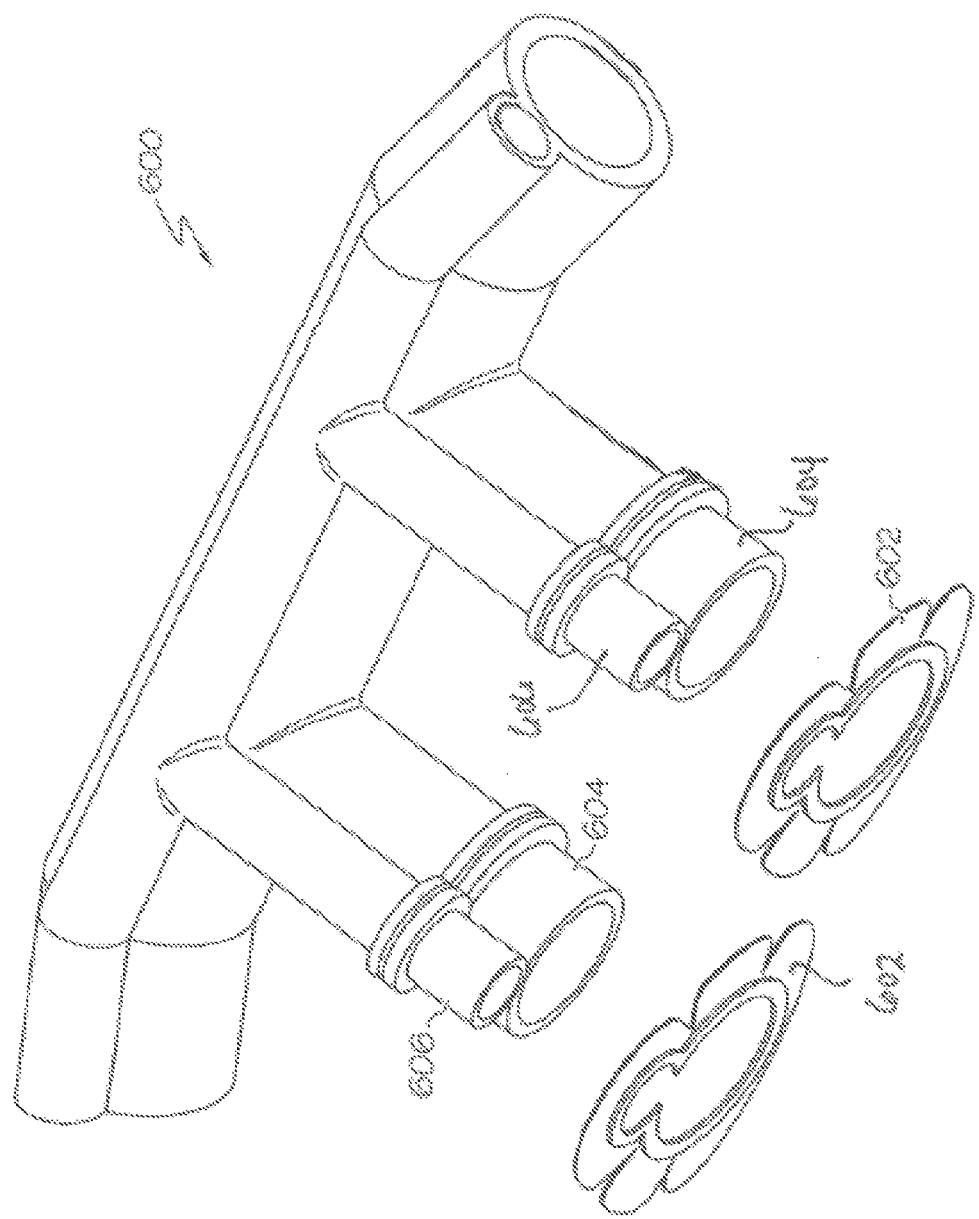
FIG. 6 is another perspective view of a dual lumen nasal cannula with a flange retention structure for attachment of flanges, which is constructed in accordance with an embodiment of the present invention.

FIG. 6 illustrates an exploded top perspective view of cannula 600 that is similar to the cannula 300 of FIG. 3. In this embodiment, the at least one impeder flange 602 is detached from the gas supply conduit 604 and pressure conduit 606.

In FIGS. 1-6, the impeder flanges (e.g., 102, 202, 302 and 402) are shown located at about ⅓ the length of the cannula length from its tip. Within this disclosure, an impeder flange can be placed anywhere on the cannula (e.g., 104, 204, 304 and 4040 where it will act to impede the egress of gas flow from the nostrils of a patient. The flange may be placed outside of the nares where it may act in a similar manner to a flap valve.

Many patients and especially many ill patients are mouth breathers, and nasal cannula may not be as effective with these patients. An oral interface for delivery of HFT can benefit these patients. Illustrated in FIGS. 7, 8 and 9 are oral interfaces for HFT.

Figure 7:
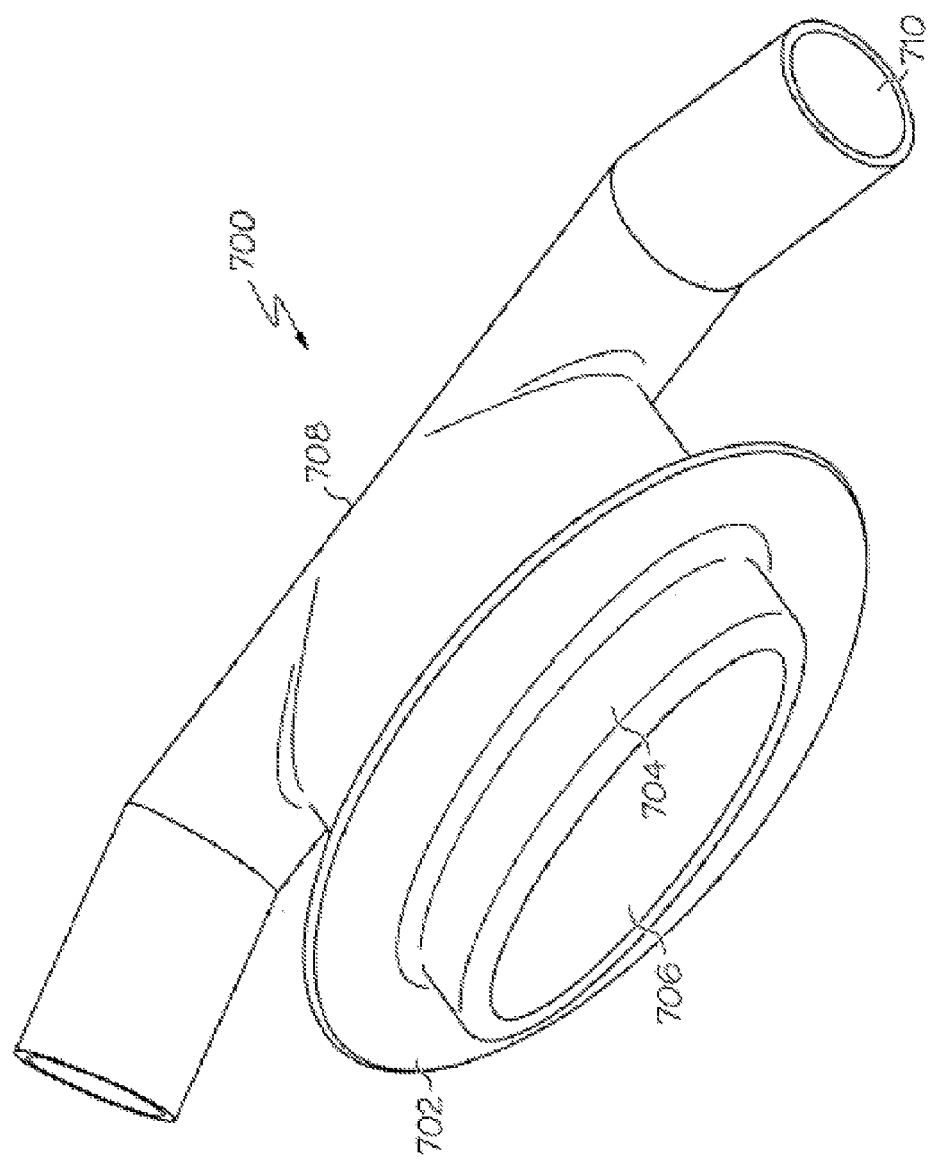
FIG. 7 is a perspective view of an oral interface for delivery of respiratory gases, which is constructed in accordance with an embodiment of the present invention.

FIG. 7 illustrates an oral interface without the use of a pressure sensor or port. Oral interface 700 can include an interface body 708 that includes a hollow elongated tubular base portion that can include a central portion, a first end portion and a second end portion. The first and second end portions can be angled relative to the central portion as illustrated in FIG. 7. Oral interface 700 further can include an oral flange 702 to provide assistance in retaining the oral interface 700 in the mouth of a patient. The oral flange 702 can be continuous as illustrated or discontinuous, e.g., lobulated, slitted or sectioned. The oral flange can be affixed to an oral cannula insert 704 of the oral interface opening 706. As illustrated in FIG. 7, the interface body 708 can have a gas supply conduit 710 at each end of interface body 708. In other embodiments, a single gas supply conduit 710 also can be used.

Figure 8:
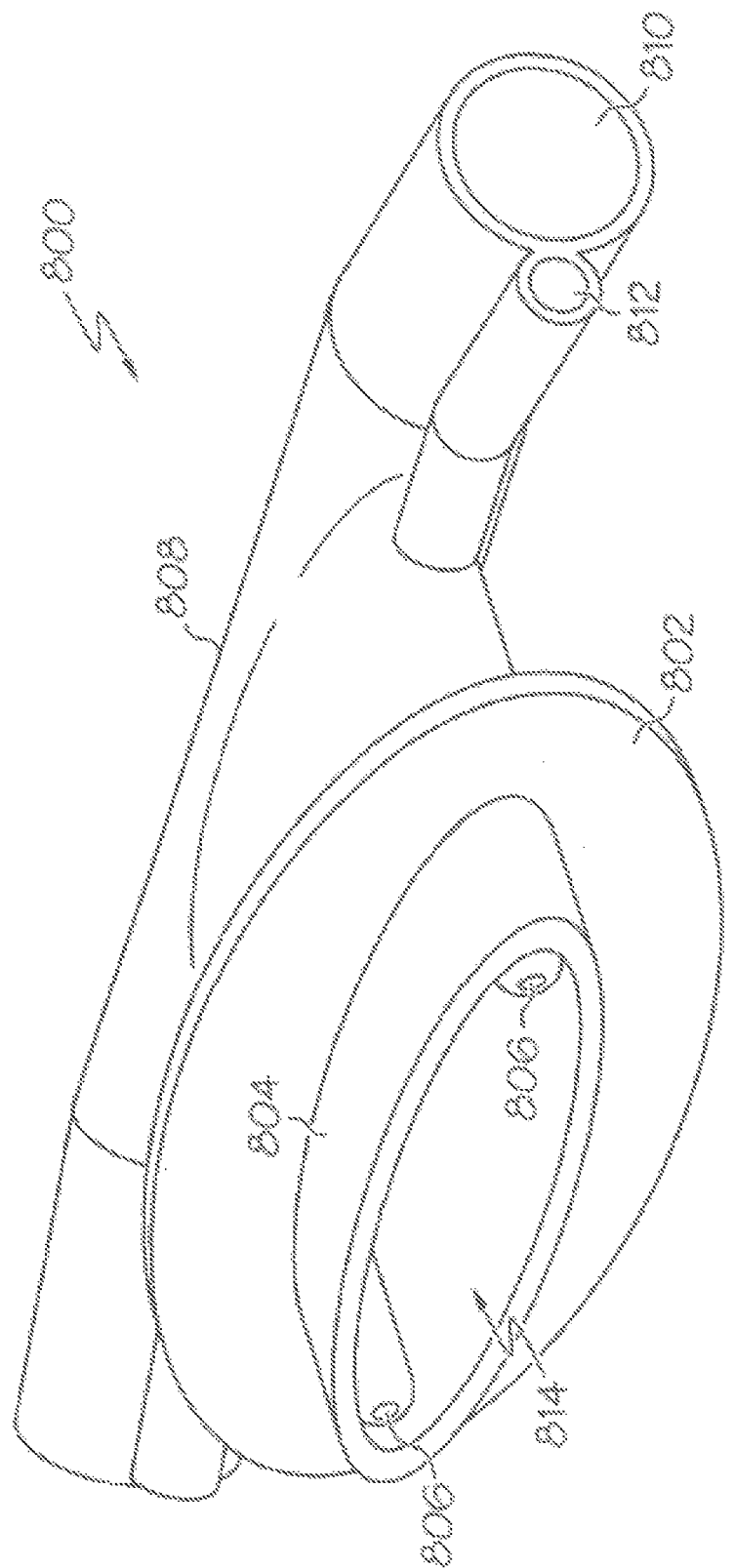
FIG. 8 is a perspective view of an oral interface for delivery of respiratory gases that includes pressure orifices, which is constructed in accordance with an embodiment of the present invention.

FIG. 8 illustrates oral interface 800 that has pressure ports or orifices 806. Oral interface 800 can include an interface body 808 that includes a hollow elongated tubular base portion that can include a central portion, a first end portion and a second end portion. The first and second end portions can be angled relative to the central portion as illustrated in FIG. 8. Oral interface 800 further can include an oral flange 802 to provide assistance in retaining the oral interface 800 in the mouth of a patient. The oral flange 802 can be continuous as illustrated or discontinuous, e.g., lobulated, slitted or sectioned. The oral flange 802 can be affixed to an oral cannula insert 804 of the oral interface opening 806. As illustrated in FIG. 8, the interface body 808 can have a gas supply conduit 810 and a pressure conduit 812 at each end of interface body 808. As illustrated in FIG. 8, the pressure ports or orifices 806 can be inset inside the oral interface opening 814, which can be used to protect the pressure lumens or conduits 812 from being occluded with fluid or by the tongue of a patient. In FIG. 8, the port 806 can be a conduit to a sensor (not shown). In embodiments, a sensor can be placed in the oral interface opening. In other embodiments, a single gas supply line and pressure sensor line can be used in other configurations of oral interface 800.

Figure 9:
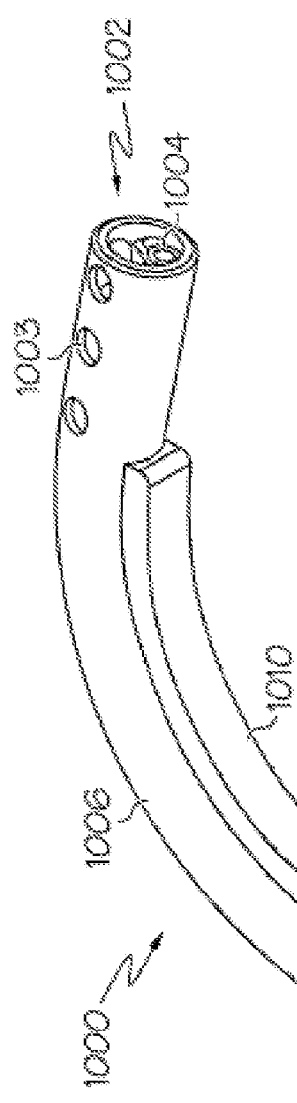
FIG. 9 is a perspective view of a dual lumen oral interface for delivery of respiratory gases to the oral cavity that includes a shaping wire, which is constructed in accordance with an embodiment of the present invention.
Figure 10:
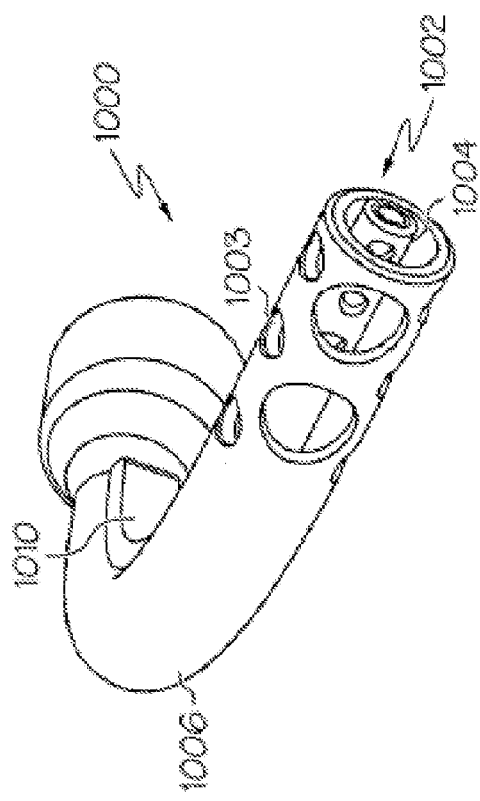
FIG. 10 is another perspective view of a dual lumen oral interface for delivery of respiratory gases to the oral cavity that includes a shaping wire, which is constructed in accordance with an embodiment of the present invention.
Figure 11:
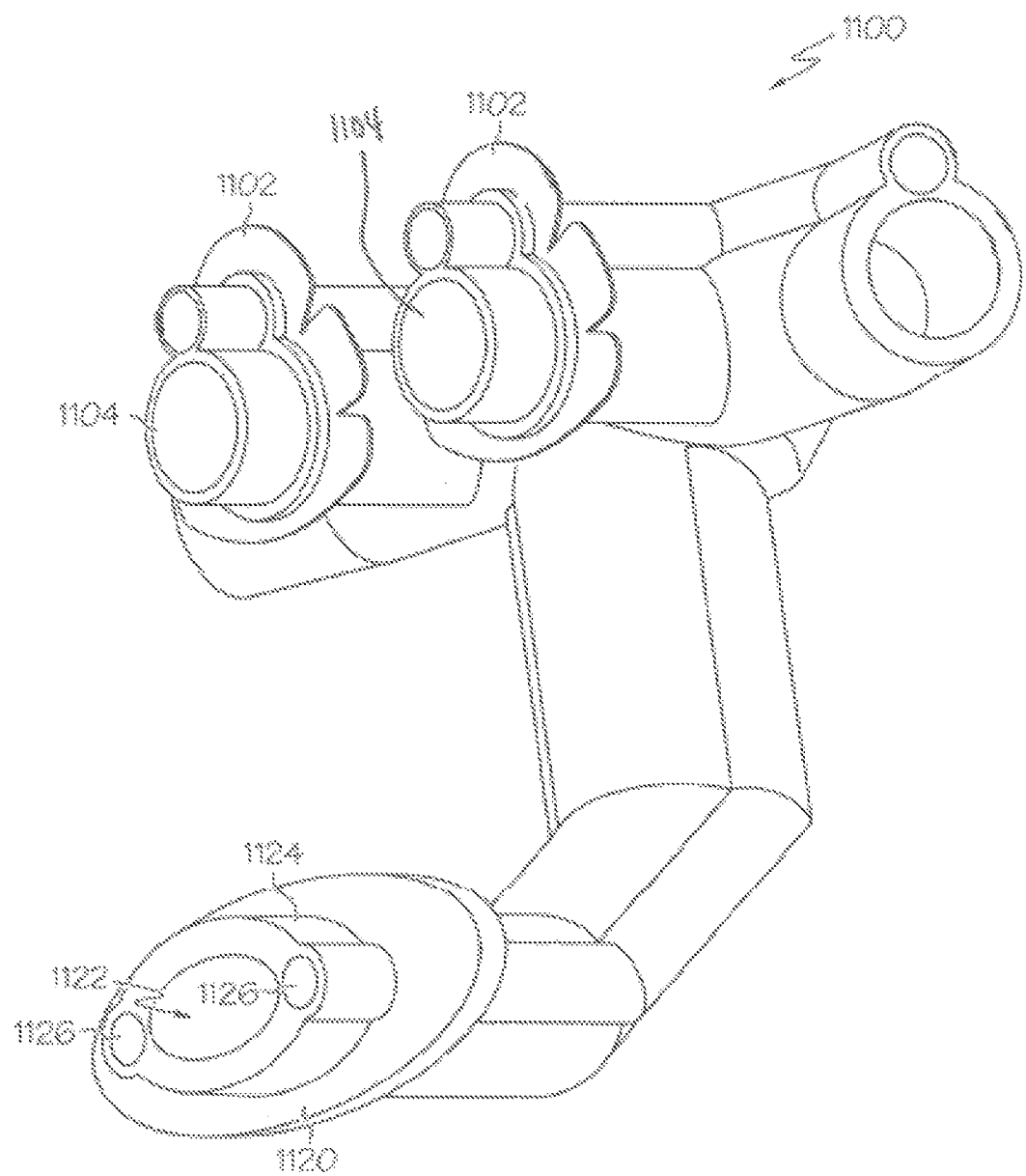
FIG. 11 is a perspective view of a combined oral and nasal interface for delivery of respiratory gases that includes pressure orifices for both the oral cavity and for the nares, which is constructed in accordance with an embodiment of the present invention.
Figure 12:
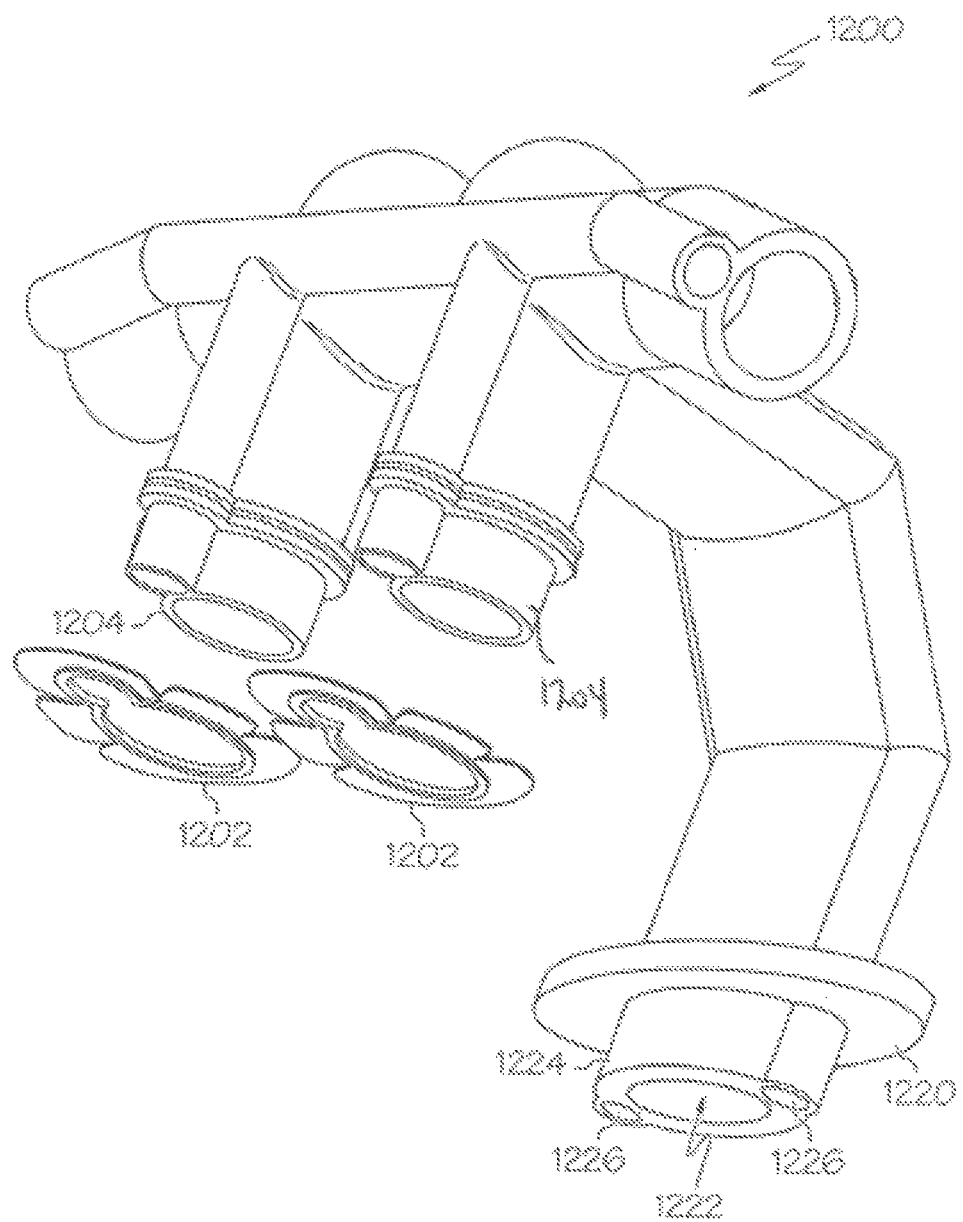
FIG. 12 is perspective view of a combined oral and nasal interface for delivery of respiratory gases that includes pressure orifices for both the oral cavity and for the nares, and has attachable flanges for the nasal cannula, which is constructed in accordance with an embodiment of the present invention.
Figure 13:
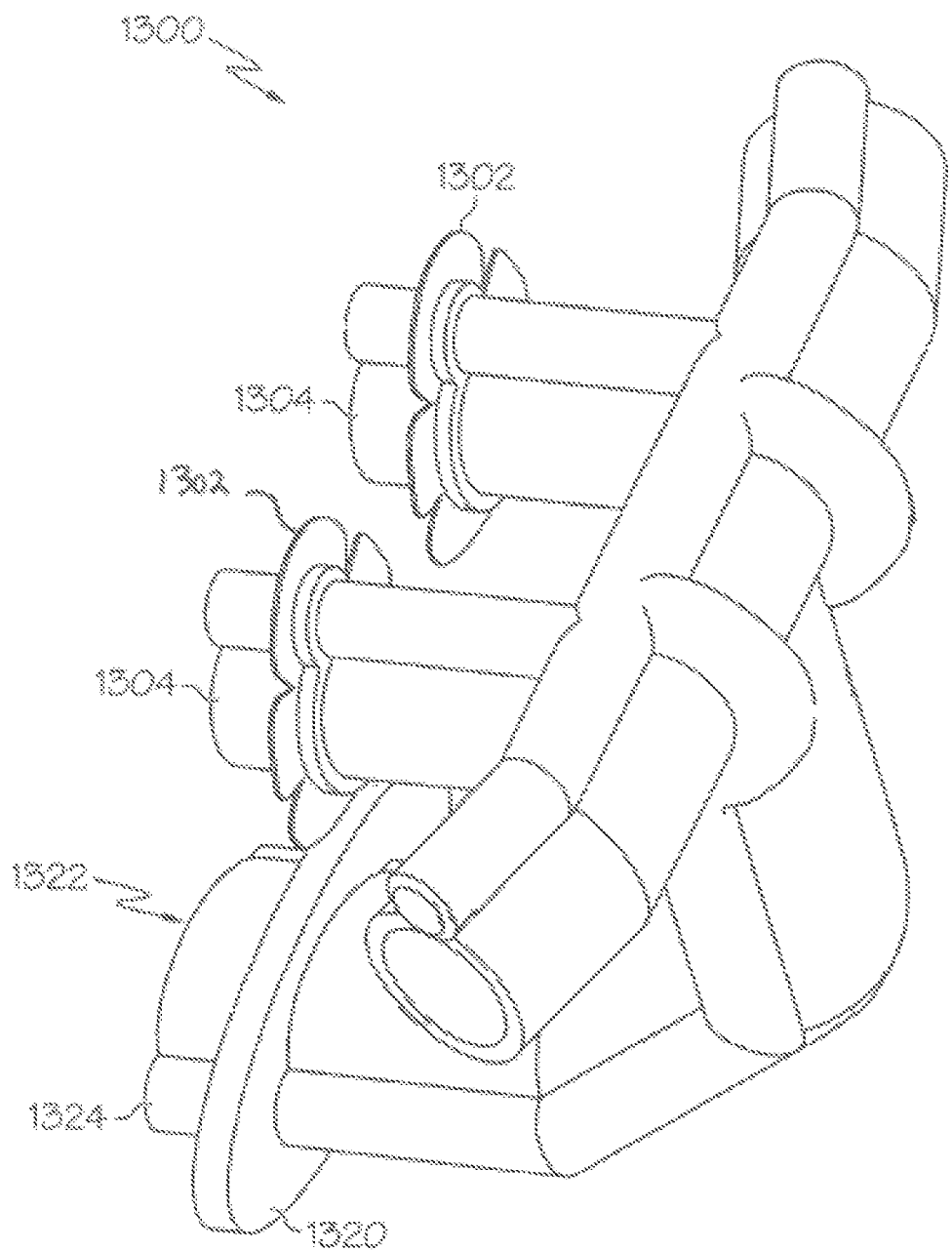
FIG. 13 is top rear perspective view of a combined oral and nasal interface for delivery of respiratory gases that includes pressure orifices for both the oral cavity and for the nares, which is constructed in accordance with an embodiment of the present invention.

FIG. 9 illustrates an oral interface 1000 designed to flex and curve to allow a head section of the oral interface 1000 to lay on the side of the mouth, or in the buccal gutter. Oral interface 1000 can include a head section 1002, a gas delivery diffuser 1003 and a pressure orifice 1004. The head section 1002 of oral interface 1000 can include a diffuser 1003 which is slotted or vented to allow a large flow of gases even if partially occluded by mucous membranes. The oral interface 1000 further can include a gas supply conduit 1006 that runs parallel to a pressure conduit 1008. The oral interface 1000 can include a shaping wire 1010 that runs parallel to the gas supply conduit 1006 and pressure conduit 1008. The shaping wire 1010 can be used to shape the oral interface 1000 in to various shapes, e.g., a J-shape or U-shape, to fit into the mouth of a patient. In this embodiment, the oral interface 1000 can be placed into the oral cavity of a patient. As illustrated in FIG. 10, the shaping wire 1010 allows the oral interface 1000 to be bent to wrap around the cheek, which allows the oral interface 1000 to lay in the gutter between the buccal surface of the cheek and the alveolar ridge (i.e., gums and teeth). The gas delivery diffuser 1003 can allow the gas to freely enter the mouth of the patient, even though some of the surface of the gas delivery diffuser 1003 may be occluded by contact with the mucosa. The gas delivery head 1002 further can include a pressure port or orifice 1004 that can be contained within the gas delivery diffuser 1003 to monitor airway pressure variation. In embodiments, the supply conduit 1006 and the pressure conduit 1008 of oral interface 1000 can be pre-shaped, for example as in a U-shape, to fit the mouth. In embodiments, a flange may also be placed to help secure the interface. The interface also can be made without a pressure sensor or port.

Figure 14:
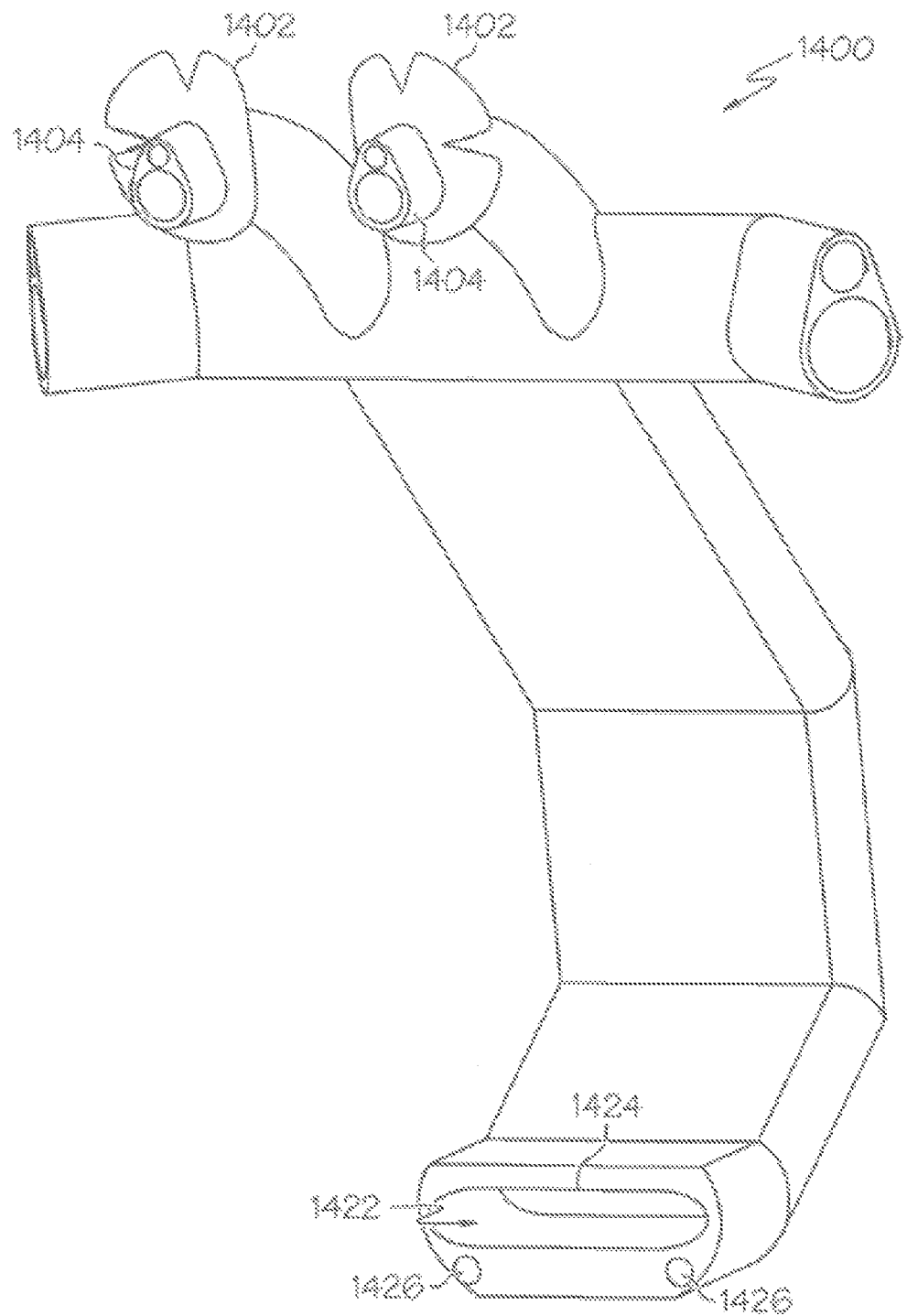
FIG. 14 is a perspective view of a combined oral and nasal interface for delivery of respiratory gases that includes pressure orifices for both the mouth and for the nares, which is constructed in accordance with an embodiment of the present invention; and, FIG. 15 is a perspective view of a combined oral and nasal interface for delivery of respiratory gases that includes pressure orifices for both the mouth and for the nares, which is constructed in accordance with an embodiment of the present invention.
Figure 15:
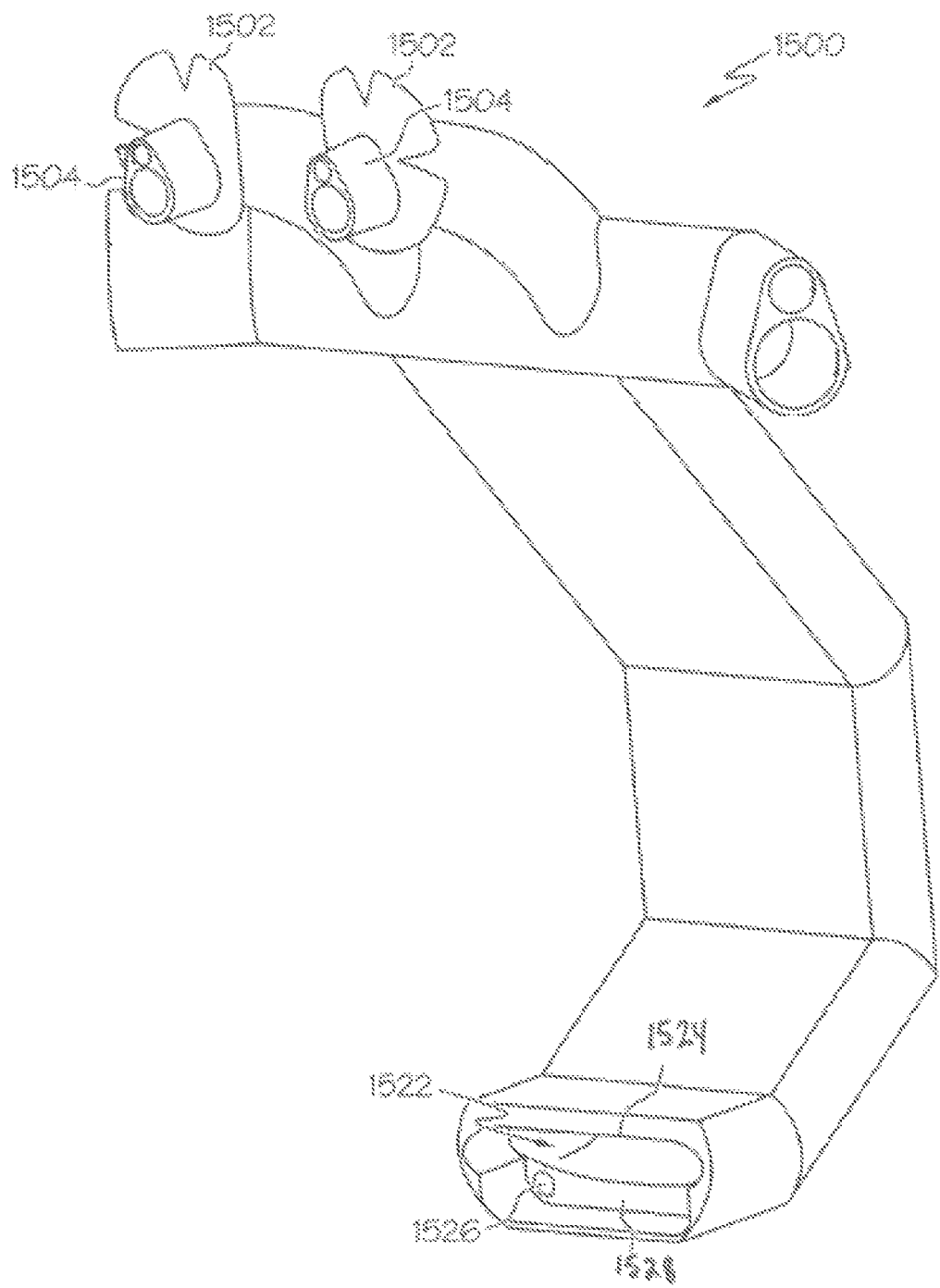

Illustrated in FIGS. 11 through 15 are combination patient interfaces that supply gas to both the nose and the mouth of a patient. The mouthpiece section has pressure ports in these figures; however the mouthpiece section may also be made without the pressure sensing area. The oral flange 1120, 1220, 1320 on the mouthpiece section 1124, 1224, 1324 can help keep the mouthpiece positioned in front or behind the teeth or alveolar ridge. As illustrated in FIGS. 14 and 15, the mouthpiece 1424, 1528 can be made without the flange. In embodiments, the mouthpiece 1124, 1224, 1324, 1424, 1528 can be made with a partial flange, or the mouthpiece can be short enough that it does not enter the mouth but merely points towards the mouth of the patient. Nasal flanges 1102, 1202, 1302, 1402, 1502 can be attachable flanges, similar to the flange 402 in FIG. 4, and use a flange retention structure e.g., a flange retention connector as illustrated in FIG. 4. In other embodiments the nasal interfaces can be manufactured with the flanges 1102, 1202, 1302, 1402, 1502. As illustrated in FIG. 15, the pressure ports or orifices 1526 can be located within a mouthpiece cavity 1524 to aid in the avoidance of mucus and other respiratory fluids clogging or partially obscuring the pressure ports or orifices 1526.

While several embodiments of the disclosure have been described and shown in the figures, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit the disclosure.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims, which are to be accorded with the broadest interpretation so as to encompass all such modifications and similar structures.

Therefore, the above-described embodiments should be regarded as illustrative rather than restrictive. Accordingly, it should be appreciated that variations to those embodiments can be made by those skilled in the art without departing from the scope of the nasal mask assembly as defined by the following claims.

We claim:

1. A nasal cannula for delivery of respiratory gases supplied from a respiratory gas delivery system, the nasal cannula comprising:
   at least two nasal inserts, wherein at least one nasal insert is structured to allow the respiratory gases to be supplied through a lumen and exhaled gases to be substantially exhausted about at least one flange during use; and
   the at least one flange coupled to at least one nasal insert, the at least one flange adapted to position within a nasal passage and having a non-sealing structure that avoids creating a seal in the nasal passage, the at least one flange adapted to partially impede the egress of respiratory gasses delivered to an upper airway of a patient, wherein the at least one flange includes a top surface defining a corresponding top surface area; and
   wherein the at least one flange further includes at least one slot defining a corresponding implicit surface area, the top surface area of the top surface being substantially greater than the implicit surface area of the at least one slot.

2. The nasal cannula of claim 1, wherein the non-sealing structure is a lobulated flange.

3. The nasal cannula of claim 1, wherein the top surface of the flange is adapted to remain contactless with the inside walls of the nostril during use.

4. The nasal cannula of claim 1, wherein the flange further includes a side surface configured to partially contact the inside walls of the nostril during use.

5. A nasal cannula for delivery of respiratory gases supplied from a respiratory gas delivery system, the nasal cannula comprising:
   at least two nasal inserts, wherein at least one nasal insert is structured to allow the respiratory gases to be supplied through a lumen and exhaled gases to be substantially exhausted about at least one flange during use;
   the at least one flange coupled to at least one nasal insert, the at least one flange adapted to position within a nasal passage and having a non-sealing structure that avoids creating a seal in the nasal passage, the at least one flange adapted to partially impede the egress of respiratory gasses delivered to an upper airway of a patient, wherein the at least one flange includes a top surface defining a corresponding top surface area,
   wherein the at least one flange further includes at least one slot defining a corresponding implicit surface area, the top surface area of the top surface being substantially greater than the implicit surface area of the at least one slot; and
   wherein the flange does not include a lumen to deliver the supplied respiratory gases from the respiratory gas delivery system.

6. The nasal cannula of claim 5, wherein the non-sealing structure is a lobulated flange.

7. The nasal cannula of claim 5, wherein the top surface is adapted to remain contactless with the inside walls of the nostril during use.

8. The nasal cannula of claim 5, wherein the flange further includes a side surface configured to partially contact the inside walls of the nostril during use.

9. A nasal cannula for delivery of respiratory gases supplied from a respiratory gas delivery system, the nasal cannula comprising:

at least two nasal inserts, wherein at least one nasal insert is structured to allow the respiratory gases to be supplied through a lumen and exhaled gases to be substantially exhausted about at least one flange during use; and the at least one flange coupled to at least one nasal insert, the at least one flange adapted to position within a nasal passage and having a non-sealing structure that avoids creating a seal in the nasal passage, the at least one flange adapted to partially impede the egress of respiratory gasses delivered to an upper airway of a patient, wherein the at least one flange includes a top surface defining a corresponding top surface area, wherein the at least one flange further includes at least one slot defining a corresponding implicit surface area, the top surface area of the top surface being substantially greater than the implicit surface area of the at least one slot; and wherein the top surface of the flange is substantially parallel to a top surface of the lumen of the at least one nasal insert.

10. The nasal cannula of claim 9, wherein the at least one nasal insert has two lumens.

11. A nasal cannula for delivery of respiratory gases supplied from a respiratory gas delivery system, the nasal cannula comprising:

at least two nasal inserts, wherein at least one nasal insert is structured to allow the respiratory gases to be supplied through a lumen and exhaled gases to be substantially exhausted about at least one flange during use;

the at least one flange coupled to at least one nasal insert, the at least one flange having a non-sealing structure that avoids creating a seal in a nasal passage, the at least one flange adapted to partially impede the egress of the respiratory gasses delivered to an upper airway of a patient during use, wherein the at least one said flange has at least one portion that extends a first distance from an external circumference of the at least one nasal insert that is greater than the thickness of the at least one flange, where the thickness of the at least one flange is measured in a direction parallel to a top surface of a lumen of the at least one nasal insert; and wherein the flange is adapted to fit within the nostril of a patient.

12. The nasal cannula of claim 11, wherein the nasal insert includes an upper nasal insert portion and a lower nasal insert portion divided by the flange.

13. The nasal cannula of claim 11, wherein the flange does not include a lumen to deliver the supplied respiratory gases from the respiratory gas delivery system.

14. The nasal cannula of claim 11, wherein the flange and the nasal insert are integral.

15. The nasal cannula of claim 11, wherein the flange has at least one slot.

16. The nasal cannula of claim 11, wherein the at least one nasal insert has two lumens.

17. The nasal cannula of claim 11, wherein the top surface is adapted to remain contactless with the inside walls of the nostril during use.

18. The nasal cannula of claim 11, wherein the flange further includes a side surface adapted to partially contact the inside walls of the nostril during use.

19. A nasal cannula for delivery of respiratory gases supplied from a respiratory gas delivery system, the nasal cannula comprising:

at least two nasal inserts, wherein at least one nasal insert is structured to allow the respiratory gases to be supplied through a lumen and exhaled gases to be substantially exhausted about at least one flange during use;

the at least one flange coupled to at least one nasal insert, the at least one flange having a non-sealing structure that avoids creating a seal in a nasal passage, the at least one flange adapted to partially impede the egress of respiratory gasses delivered to an upper airway of a patient, wherein the at least one flange has at least one portion that extends a first distance from an external circumference of the at least one nasal insert that is greater than the thickness of the at least one flange, where the thickness of the at least one flange is measured in a direction parallel to a top surface of a lumen of the at least one nasal insert; and wherein the flange and the nasal insert are integral.

20. The nasal cannula of claim 19, wherein the flange is configured to fit within the nostril of a patient.

21. The nasal cannula of claim 19, wherein the nasal insert has an upper nasal insert portion and a lower nasal insert portion that are divided by the flange.

22. The nasal cannula of claim 19, wherein the flange does not include a conduit to deliver the supplied respiratory gases from the respiratory gas delivery system.

23. The nasal cannula of claim 19, wherein the flange has at least one slot.

24. The nasal cannula of claim 19, wherein the at least one nasal insert has two lumens.

25. The nasal cannula of claim 19, wherein the top surface is configured to remain contactless with the inside walls of the nostril during use.

26. The nasal cannula of claim 19, wherein the flange further includes a side surface configured to partially contact the inside walls of the nostril during use.

* * * * *